United States Patent

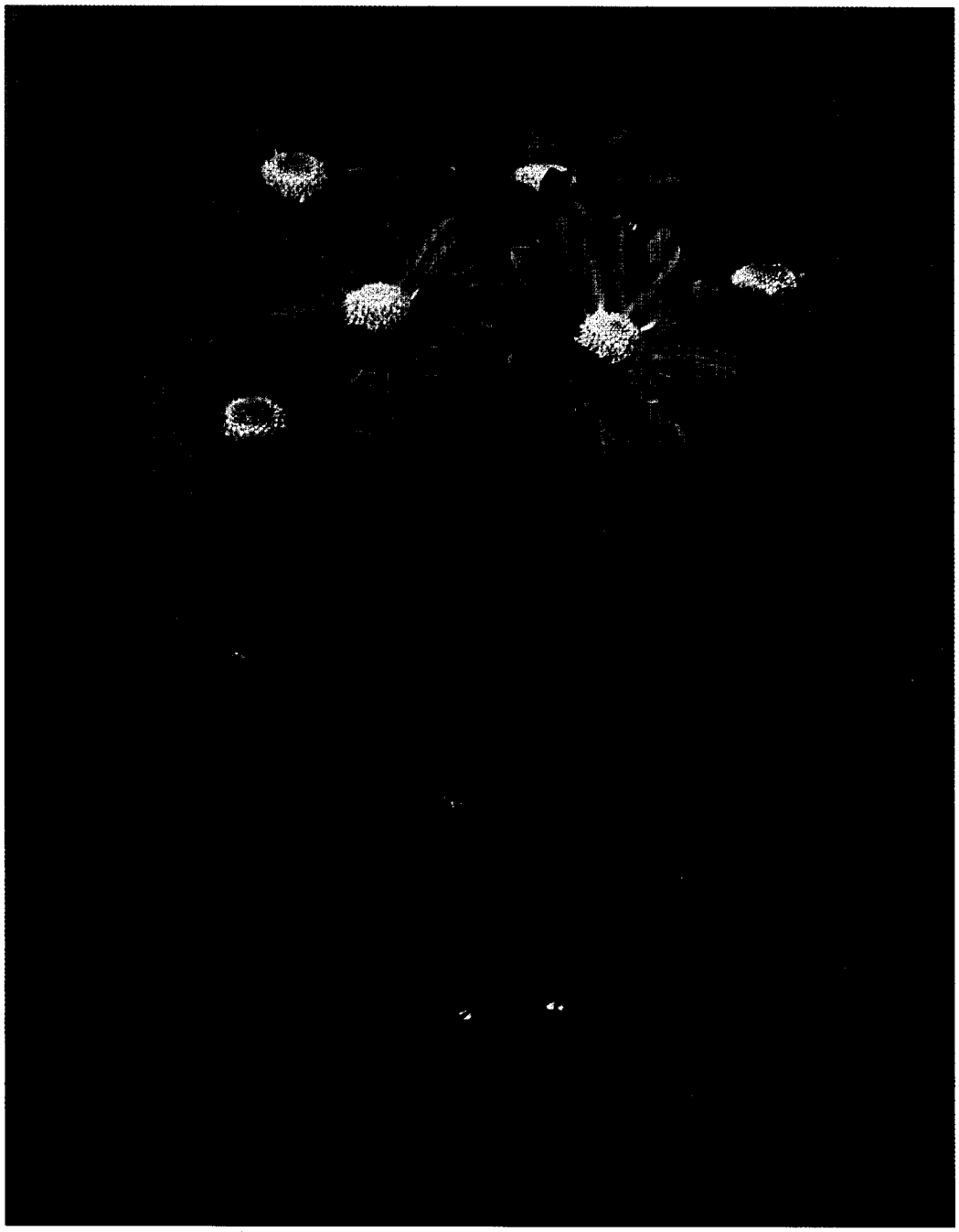

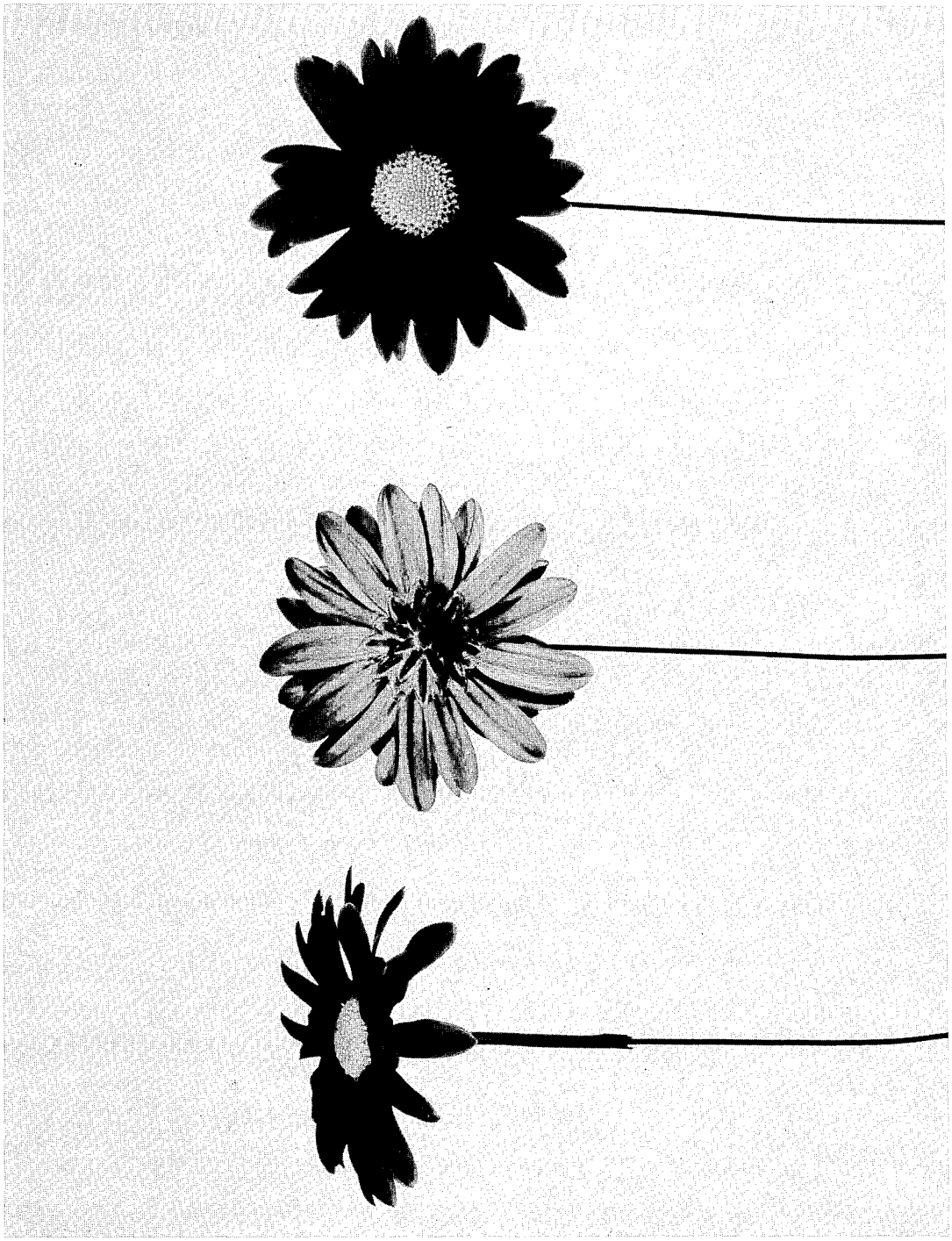

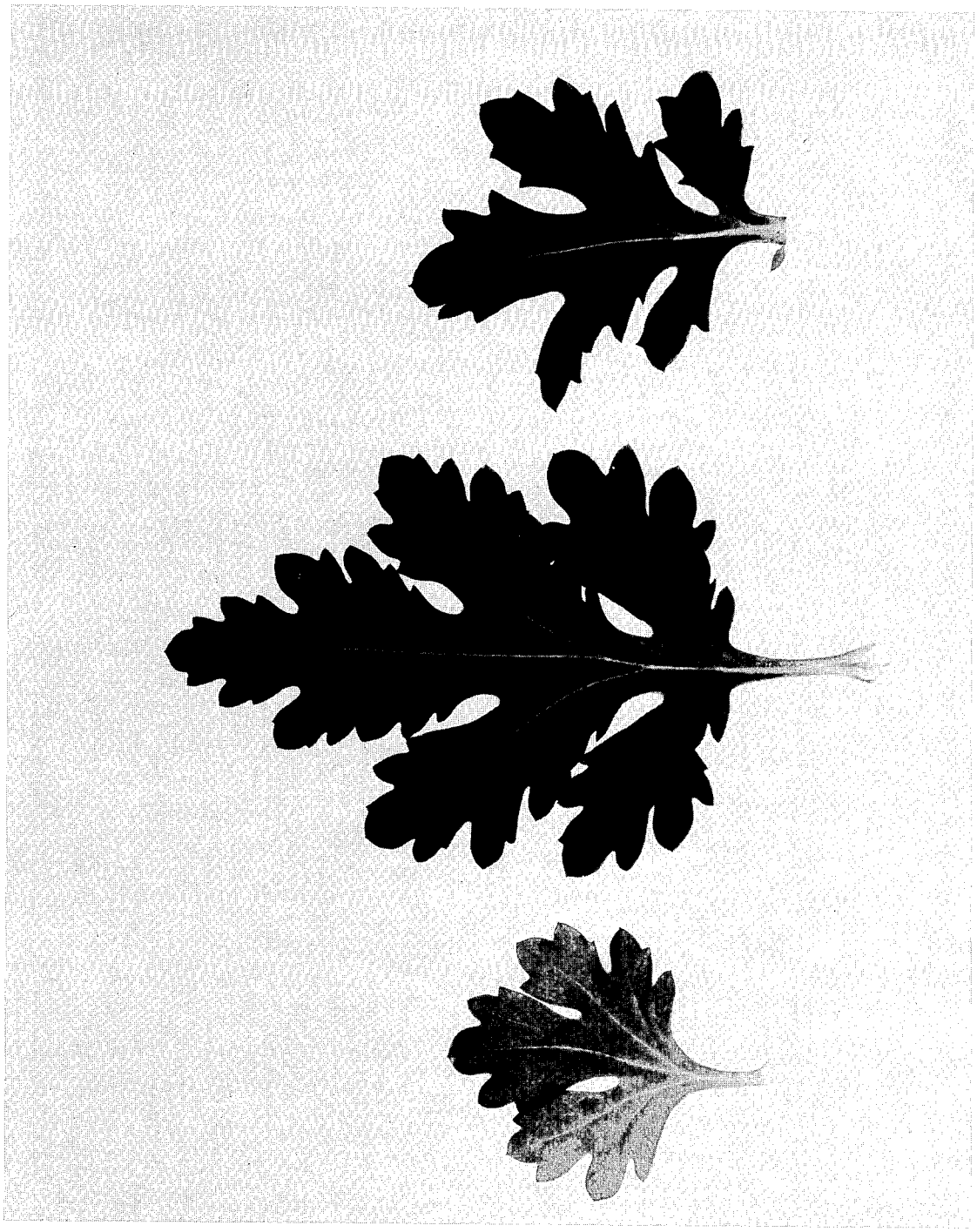

Plant Pat. 3,947
Patented Aug. 24, 1976

3,947
CHRYSANTHEMUM PLANT

Walter H. Jessel, Jr., Doylestown, and William E. Duffett, Akron, Ohio, assignors to Yoder Brothers, Inc., Barberton, Ohio Filed Aug. 4, 1975, Ser. No. 601,633
Int. Cl.[2] A01H 5/00
U.S. Cl. Plt.—74 1 Claim The present invention comprises a new and distinct cultivar of *Chrysanthemum morifolium*, Ramat., hereinafter referred to by the cultivar name Firepower (#72206001).

Firepower was originated from a cross made in a controlled breeding program in Barberton, Ohio in the year 1971. The female, or seed parent, was Nero (#21700E01; unpatented; commercially available), a red-bronze daisy of parentage unknown to the present inventors. The male, or pollen parent, was Rebel (#56788001; unpatented; commercially available), a red-bronze daisy originated by the present inventors from a cross between #52502001 (unnamed seedling and #53278011 (unnamed seedling). Both parents of Rebel were products of the breeding program of the present inventors.

Firepower is a product of a planned breeding program which had the objective of creating cultivars with daisy type inflorescence, with intense red and red-bronze inflorescence color, with minimal color oxidation, with tall plant height, and with efficient nine and ten week flowering response, specifically for the fall, winter and spring flowering periods. These traits in combination were not present in previously available commercial cultivars.

Firepower was discovered and selected as a flowering plant within the progeny of the stated cross by William E. Duffett and Walter H. Jessel, Jr. on Nov. 16, 1972 in a controlled environment in Barberton, Ohio.

The first act of asexual reproduction of Firepower was accomplished when vegetative cuttings were taken from the initial selection in December 1972 in a controlled environment in Barberton, Ohio by a technician working under formulations established and supervised by William E. Duffett and Walter H. Jessel, Jr. Horticultural examination of selected units initiated April 10, 1974 has demonstrated that the combination of characteristics as herein disclosed for Firepower are firmly fixed and are retained through successive generations of asexual reproduction .

Firepower has not been observed under all possible environments. The phenotype may vary significantly with variations in environmental conditions such as temperature, light itensity, and daylength. The following observations, measurements, and comparisons describe plants grown in a greenhouse in Barberton, Ohio under environmental conditions which approximate those generally used in commercial practice, as described in Chart A and Chart B which appear at the end of the present specification.

The following traits have been repeatedly observed and are determined to be basic characteristics of Firepower which in combination distinguish this chrysanthemum as a new and distinct cultivar:

(1) Flat inflorescence form which reflexes slightly with age.

(2) Daisy inflorescence type.

(3) Diameter across face of inflorescence up to 4.0 inches at maturity.

(4) Red ray floret color, with blue highlights.

(5) Medium green disc floret color at immature, unopened stage.

(6) Minimal pollen development.

(7) Semi-upright branching habit.

(8) Tall plant height.

(9) High percentage gradeout in top grades (SAF standards).

The accompanying photographic drawings show typical inflorescence and foliage characteristics of Firepower. Some difficulty in obtaining accurate representation of ray floret color was encountered. The actual color has more blue overtones than depicted in Sheet 1. Sheet 2 is a black and white photograph showing three views of the inflorescence of Firepower. Sheet 3 is a black and white photograph of the foliage of Firepower at three stages of growth.

Well known, commercially available cultivars with which Firepower may appropriately be compared are Red Galaxy (#46331B07; unpatented), and the parental cultivars, Nero and Rebel. Reference is made to attached Chart C which compares certain characteristics of the above mentioned cultivars with the same characteristics of Firepower. General comparisons are as follows.

In comparison to Nero, Firepower has different ray floret color and longer peduncle length. The immature disc floret color, flowering response period, inflorescence form, inflorescence type, and percentage gradeout in top grades (SAF standards) of Firepower are similar to those of Nero.

In comparison to Rebel, Firepower has different ray floret color, different immature disc floret color, and shorter flowering response period. The inflorescence form, inflorescence type, and percentage gradeout in top grades (SAF standards) of Firepower are similar to those of Rebel.

In comparison to Red Galaxy, Firepower has different ray floret color, different immature disc floret color, shorter flowering response period, and higher percentage gradeout in top grades (SAF standards). The inflorescence form and inflorescence type of Firepower are similar to those of Red Galaxy.

In the following description, color references are made to The Munsell Limit Color Cascade, 1972 edition. The color values were determined between 12:30 P.M. and 1:00 P.M. on April 8, 1975 under 150 foot candle light intensity.

BOTANICAL CLASSIFICATION

*Chrysanthemum morifolium*, Ramat., cv Firepower.

I. Inflorescence

A. Capitulum:
- *Form.*—Flat.
- *Type.*—Daisy.
- *Permanence.*—10 to 12 days.
- *Diameter across face.*—3.0 to 4.0 inches.

B. Corolla of ray florets:
- *Texture (adaxial).*—Glabrous.
- *Appearance and form.*—Ligulate.
- *Arrangement.*—Whorled on receptacle.
- *Persistence.*—Resists shatter.
- *Color (abaxial).*—Approximately 29–6 to 32–11 streaked with 37–15.

*Color (adaxial).*—Approximately 29–4 to 32–5 streaked with 42–13.

*Venation.*—Prominent.
*Margin.*—Moderately serrated.

CHART A—AVERAGE GREENHOUSE CHRYSANTHEMUM ENVIRONMENTS USED FOR BARBERTON, OHIO

| Season | Temperatures used (°F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

C. Corolla of Disc Florets:
*Appearance.*—Gameopetalous; tubular; 5-lobed.
*Color.*—23–10 to 27–6.
D. Reproductive organs:
*Androecium.*—Scant; present disc florets only; syngenesious stamen; scant pollen.
*Gynoecium.*—Present both ray and disc florets; inferior, bicarpellate ovary; single style; 2-lobed stigma.

II. Plant

A. *General appearance.*—Semi-upright; tall.
B. *Duration and Texture.*—Herbaceous; perennial.
C. *Foliage:*
*Color (abaxial).*—Approximately 21–13 to 21–16.
*Color (adaxial).*—Approximately 21–12 to 21–14 overlaid with white.
*Shape.*—Spatulate; deeply lobed.
*Texture.*—Glabrous; leathery.
*Arrangement.*—Alternate.

CHART B

INTENSITY OF DIRECT SOLAR RADIATION

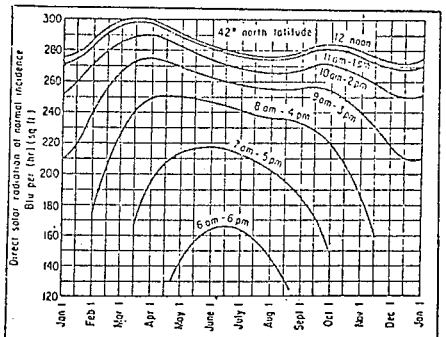

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF FIREPOWER, NERO, REBEL, AND RED GALAXY

| Cultivar | Ray floret color | Immature disc floret color | Flowering response period | Inflorescence form and type | Gradeout (SAF) | Peduncle length |
|---|---|---|---|---|---|---|
| Firepower | Red | Green | 9 weeks | Flat daisy | High | Long. |
| Nero | Red bronze | do | do | do | do | Short. |
| Rebel | Dark red | Yellow | 11 weeks | do | do | Long. |
| Red galaxy | Red bronze | do | do | do | Medium | Do. |

NOTE.—Comparisons made of flowered plants grown in a greenhouse in Barberton, Ohio under conditions as described in Chart A and Chart B.

We claim:

1. A new and distinct form of chrystanthemum plant known by the cultivar name Firepower and particularly characterized by the combined characteristics of flat inflorescence form which reflexes slightly with age; daisy inflorescence type; diameter across face of inflorescence up to 4.0 inches at maturity; red ray floret color, with blue highlights; medium green disc floret color at immature, unopened stage; minimal pollen development; semi-upright branching habit, tall plant height, and its high percentage gradeout in top grades (SAF standards).

No references cited.

ROBERT E. BAGWILL, Primary Examiner